United States Patent
Holtkamp, Jr.

[11] Patent Number: 5,704,162
[45] Date of Patent: Jan. 6, 1998

[54] FRAGRANCE EMITTING PLANT WATERING SYSTEM WITH FUNNEL-SHAPE POT SUPPORT

[75] Inventor: Reinhold Holtkamp, Jr., Nashville, Tenn.

[73] Assignee: International Plant Breeding AG, Bern, Switzerland

[21] Appl. No.: 514,818

[22] Filed: Aug. 14, 1995

Related U.S. Application Data

[62] Division of Ser. No. 352,078, Dec. 1, 1994, Pat. No. 5,477,640.

[51] Int. Cl.⁶ ........................................... A01G 31/02
[52] U.S. Cl. ........................................ 47/79; 47/81
[58] Field of Search ................... 47/81 N, 79 N, 47/41.01, 79, 66, 66 SC, 84; 220/408, 469

[56] References Cited

U.S. PATENT DOCUMENTS

| | | | |
|---|---|---|---|
| 1,815,676 | 7/1931 | Medveczky | 47/79 V |
| 3,481,075 | 12/1969 | Dastoli | 47/41.01 |
| 3,539,075 | 11/1970 | Bautista | 220/408 |
| 3,783,555 | 1/1974 | Deters | 47/79 V |
| 4,244,147 | 1/1981 | Geddes | 47/81 N |
| 4,858,381 | 8/1989 | Walton | 47/41.01 |
| 4,958,461 | 9/1990 | Aldrica | 47/41.01 |
| 5,282,335 | 2/1994 | Holtkamp | 47/81 N |
| 5,491,929 | 2/1996 | Peacock | 47/84 |

FOREIGN PATENT DOCUMENTS

| | | | |
|---|---|---|---|
| 3528798 | 2/1987 | Germany | 47/81 N |
| 954175 | 4/1964 | United Kingdom | 47/79 N |

*Primary Examiner*—Henry E. Raduazo
*Attorney, Agent, or Firm*—Foley & Lardner

[57] ABSTRACT

A fragrance emitting plant watering system having a bottom vase providing a reservoir for water supply for a potted plant, an air freshener cartridge supported on the vase, a cap adapted to overlie the cartridge and having a central section for supporting a plant, and wherein the cap is adjustable relative to the vase for movement between a first position in which the cap is raised to variably expose the cartridge to emit fragrance, and a second position in which the cap substantially covers the cartridge to seal said cartridge and inhibit fragrance emission.

2 Claims, 2 Drawing Sheets

FRAGRANCE EMITTING PLANT WATERING SYSTEM WITH FUNNEL-SHAPE POT SUPPORT

This application is a division of application Ser. No. 08/352,078, filed Dec. 1, 1994, and now U.S. Pat. No. 5,477,640.

BACKGROUND OF THE INVENTION

The present invention relates in general to a combination fragrance emitter and potted plant container, and in particular to a combination fragrance emitter and plant-supporting container having a self-watering capability.

Plant watering containers having self-watering features are known in the art, reference being made to U.S. Pat. Nos. 4,996,792 and 5,111,614, to Reinhold Holtkamp, Sr. The patented assembly comprises a container which serves as a liquid reservoir, with a potted plant being supported on and within the container. A watering wick extends upwardly into the pot and downwardly into the water reservoir, thereby permitting watering of the plant through capillary action. The self-watering feature has proved highly satisfactory and the container has had substantial commercial success. However, there is no fragrance emitting characteristic associated with the self-watering container.

There are a myriad of commercially available air freshener products and these vary greatly in type and function. Typical room fresheners are characterized by being relatively compact and decorative, thereby providing the desired air freshening function in an aesthetically satisfactory design or configuration. However, to the best knowledge of applicant, there has been no air freshener prior to the present invention which combines both the air freshening feature with a self-watering container capable of supporting and providing a watering system for a potted plant. Although U.S. Pat. No. 4,165,835 describes a combined fragrance dispenser and humidifier capable of receiving a relatively limited number of decorative cut flower stems, the device is primarily a humidifier and is incapable of supporting a potted plant. Moreover, the structure and arrangement of the container and fragrance emitter are distinctly different than in accordance with the present invention.

SUMMARY OF THE INVENTION

The basic objective of the present invention is to advantageously combine into a single product the feature of fragrance emission with a plant-supporting container having a water reservoir from which the supported plant can be automatically self-watered.

A further object is to provide such a combination wherein the overall configuration is aesthetically pleasing, is durable and long-lasting in construction, and can provide fragrance emission and self-watering capability for the potted plant for relatively long periods of time.

A further objective of the invention is to provide such a device wherein either the fragrance emitting capability or the self-watering feature can be replenished quickly and easily. The water supply can be replenished by simply lifting the potted plant from its support and filling the water reservoir to the desired level. The fragrance emitting substance is preferably in the form of an annular cartridge adapted to be supported by the bottom container or vase, and disposed in spaced relation around an upwardly extending neck of the vase. A cap extends over the vase and cartridge and provides support for the potted plant. The cap can be quickly and easily removed from its mounting on the vase, thereby permitting the cartridge to be operatively positioned in place, or replaced in the event the fragrance emitting substance has been spent or dissipated.

A further feature of the invention is the ability to variably adjust fragrance emission. In accordance with the invention, the cap overlying the fragrance emitting cartridge is vertically adjustable relative to the vase, preferably by a screw threaded mounting arrangement. The cap can be moved to a lower position in which it fully engages the vase and completely encloses and seals off the cartridge, or to a partially or fully open position in which the cartridge is exposed on all sides to the atmosphere to emit fragrance into the room. The cap can be closed for shipping or when emission of fragrance is not desired, and can be variably adjusted to the desired open position by the consumer to obtain the desired amount of fragrance emission.

In accordance with the preferred embodiment of the invention, the fragrance emitting plant watering system is characterized as comprising a bottom vase defining a reservoir for water supply for a potted plant and having a generally circular neck portion extending upwardly at the top end of the vase; an annular air freshener cartridge supported on the vase around and in spaced relation to the neck of the vase; a cap or cover overlying the cartridge and providing a supporting surface for a potted plant, and wherein the cap is mounted relative to the neck of the vase so as to be vertically adjustable with regard to the vase, thereby variably exposing the cartridge to the atmosphere so as to variably adjust fragrance emission.

These and other objects of the invention will be apparent as the following description proceeds in particular reference to the application drawings.

DETAILED DESCRIPTION OF THE PREFERRED EMBODIMENTS

Figure 1:
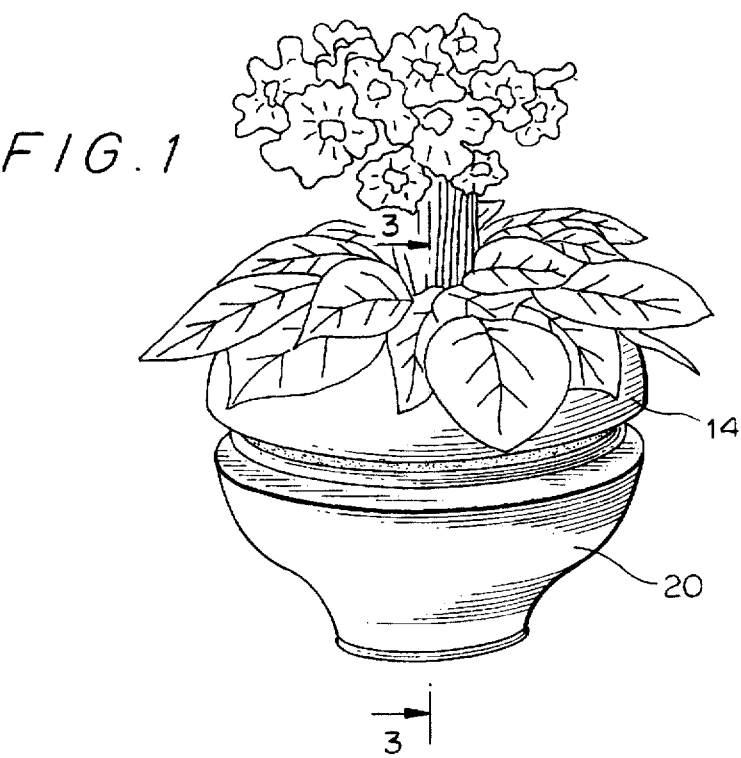
FIG. 1 is a perspective view of the preferred embodiment of the invention, showing a potted plant supported on the vase and the cap adjusted to a relatively open position.
Figure 2:
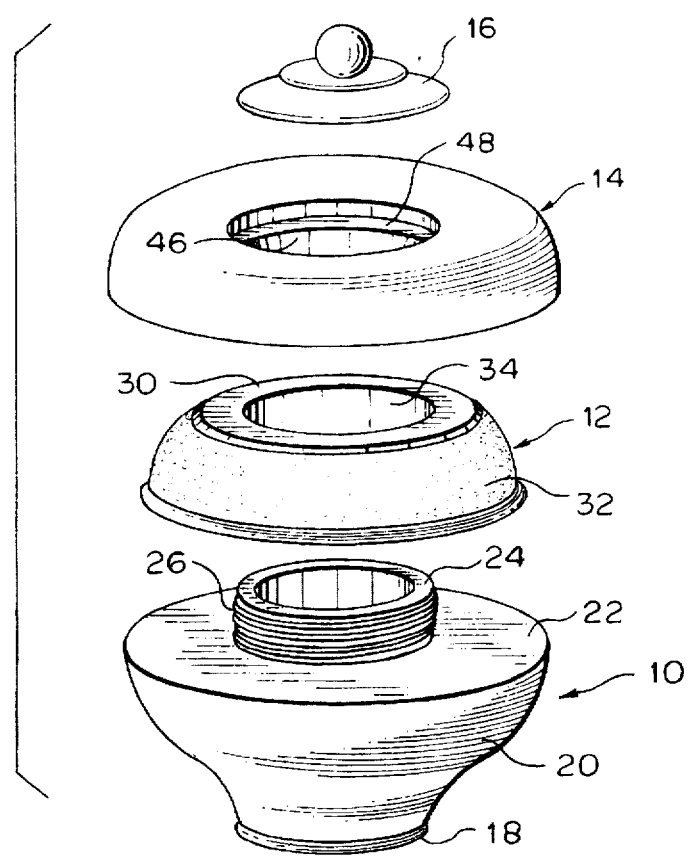
FIG. 2 is an exploded view showing the basic components of the system, with an optional cap being shown in lieu of a potted plant.

Referring now in more detail to the application drawings, wherein like parts are indicated by like reference numerals, and initially to FIGS. 1 and 2, the fragrance emitting plant watering system of the present invention comprises a vase or container generally indicated at 10, a fragrance cartridge generally indicated at 12, and a cap generally indicated at 14. In FIG. 2, a cover 16 is illustrated which can be optionally used in the absence of a potted plant, for closing the open center of the cap.

The vase includes a base 18, an upwardly enlarged body 20, a flat upper portion 22, and a reduced diameter neck 24 provided on its exterior surface with threads 26 to receive the cap 14 as will be hereinafter described.

The cartridge 12 includes a generally U-shaped casing 30 (see FIG. 3) in which is disposed a fragrance emitting substance 32, preferably in the form of a solid gel material.

The casing and gel are preferably prepackaged, and the casing is formed with a central opening 34 to permit the cartridge to be positioned loosely around the neck 24 and be supported on the flat upper portion 22 of the vase. The cap 14 is adapted to extend over the cartridge to variably enclose the same, and is vertically adjustable relative to the base as will be presently described.

Figure 3:
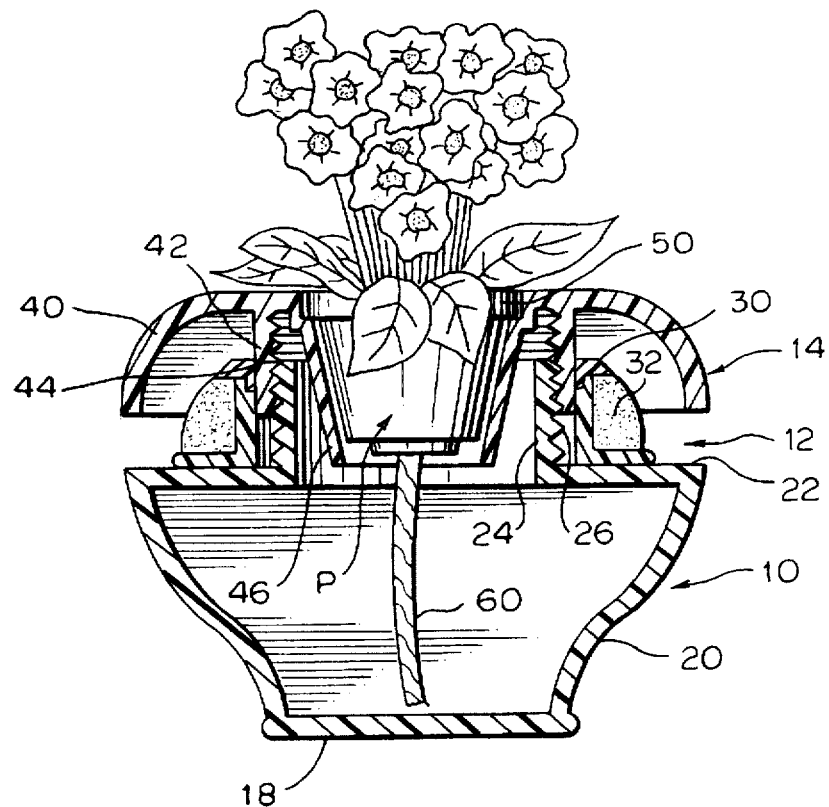
FIG. 3 is a cross-sectional view of the system, showing the cap in an elevated position to expose the fragrance cartridge.
Figure 4:
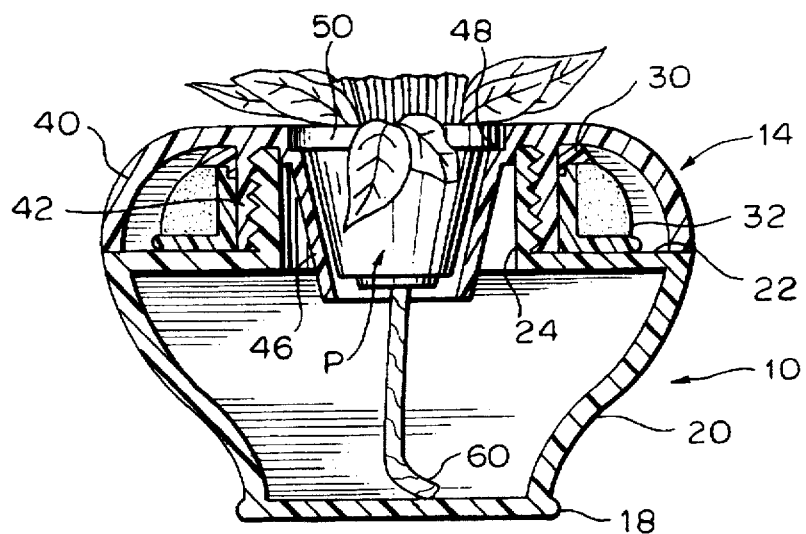
FIG. 4 is a cross-sectional view similar to FIG. 3, showing the cap in a closed position completely enclosing the cartridge, with the potted plant being shown fragmentarily.

Referring to FIGS. 3 and 4, the cap 14 includes a curved top portion 40, an annular downwardly depending skirt 42 having internal threads 44, and a generally funnel-shaped central section 46. The angularity and height of the funnel section is designed to complement the shape of the pot, and the section is formed near its top with an annular shoulder 48 adapted to be engaged by and provide support for the top flange 50 of the pot, generally indicated at P. The shoulder 48 is below the top horizontal surface of the top 40 of the cap by an amount substantially equal to the vertical dimension of the flange 50 of the pot, whereby the top of the pot is generally coplanar with the top surface, as shown in FIGS. 3 and 4. The potted plant can thus be simply dropped in the funnel-shaped section 46, which snugly receives and supports the same. It will be noted that when the pot is in position, the bottom of the section 46 extends below the pot. This arrangement serves to trap any water which may tend to accumulate near the center of the vase when and if the vase is inadvertently tipped or turned sideways during shipping or handling, thus precluding or inhibiting water from dripping out through the area in which the pot is positioned.

To render the system self-watering, a wick 60 is positioned in the growing media within the pot P and extends downwardly into the vase, terminating near or at the bottom thereof. A locking system for the wick can be provided to retain the wick in place, for example, a system as described in U.S. Pat. No. 4,932,159. However, the specific manner in which the wick is locked in place in the pot forms no part of the present invention.

The threads 26 formed on the exterior surface of the neck 24 of the vase and the threads 44 formed on the interior surface of the skirt 42 of the cap 14 are configured and dimensioned so that the cap can be threaded on the neck and vertically adjustable with regard to the top surface 22 of the vase. The internal diameter of the casing 30 of the cartridge 12 is dimensioned so that such diameter is slightly larger than the outer diameter of the skirt 42. Thus, the skirt 42 can be inserted within the cartridge and threadedly received by the neck of the vase.

The vertical adjustability of the cap relative to the vase has several advantages. When the cap is threaded down tight against the surface 22 of the vase, the cartridge is fully enclosed, as shown in FIG. 4. Since in that position the cartridge is essentially sealed, fragrance emission is precluded or greatly inhibited, thereby extending the useful life of the freshener gel. This also permits the cartridge to be in place at the time of shipping, thereby reducing the need for cartridge placement either at the point of sale or by the consumer. The fully closed position of the cover also inhibits water leakage outwardly of the unit in the event the vase is partially filled prior to shipment.

The system can be shipped with or without plant material. If plant material is separately supplied, it can be placed in the vase in an attractive display at the point of sale, or sold separately to the consumer. At the time the plant is positioned in the vase, the reservoir provided by the vase should of course be completely or partially filled with water, and the cap can be retained in its fully sealed position as shown in FIG. 4, or a partially open position as shown in FIG. 3.

To activate the air freshener, the user need merely unscrew the cap in much the same manner as a top or cap for a bottle. The cap can thus be withdrawn upwardly relative to the vase, with the amount of such movement being adjusted as desired by the user. The range of opening is controlled by the length of the engaged threads, and in order to remove the cap completely from the vase, for example, when the cartridge is to be replaced, the cap can be withdrawn completely from threaded engagement with the neck of the vase. The cartridge can then be replaced and the cap again threaded on the neck of the vase. It will be noted that the vertical adjustment or complete removal of the cap relative to the vase can be accomplished without affecting the potted plant.

In the preferred form, the casing 30 of the cartridge 12 is designed in two parts, an upper ring and a generally L-shaped lower ring, which can be snapped together after the solid gel 32 has been positioned over the lower ring. The gel per se forms no part of the present invention and can be a typical shrinking gel which holds its charge for approximately 30–60 days. It will be understood that when the cap is in a partially or fully opened position, the gel will be expended more quickly than when the cap is either fully closed or opened to a lesser extent.

As illustrated, the cap 14 is constructed in one piece, and therefore can be manufactured inexpensively. The vase is likewise preferably of one piece construction.

In the form shown, the cap 14 and particularly the funnel-shaped center section 46 is designed to receive a small miniature plant having a pot size of approximately 4–6 cm. However, it will be apparent that the vase and cap could be substantially larger in size.

In the absence of a potted plant, a cover 16 (FIG. 2) can be positioned in the central opening of the cap, with the dimension of the cover being such that it engages and is supported by the shoulder 48. The system can thus be fully closed at the top when a plant is not present, with the cover 16 providing an attractive appearance in the event the system is utilized only for air freshening purposes. This greatly expands the versatility of the product.

The dimensions of the system can be varied as desired. If the system is designed to accommodate larger potted plants than that described and illustrated, the components comprising the system will have correspondingly greater dimensions. However, the system will function in the same manner. The size and shape of the vase is such that a water storage capacity of approximately two weeks is desirably provided. The watering of the plant by capillary action ensures that continuous bottom watering is provided for, a feature that many plants, for example, African Violets, greatly prefer.

Although a solid gel is illustrated and described as the preferred freshener substance, other forms of cartridge designs having controlled release of fragrance can be utilized. One such form similarly utilizes a cartridge, but the fragrance emitting substance is liquid. In that form, the cartridge further includes a silicon paper membrane for retaining and emitting the substance, with the amount of surface space of the membrane being directly proportionate to the amount of fragrance to be emitted. In such form, a seal is preferably provided with the cartridge, and the seal can be broken by the customer at the time the air freshener is activated. In this alternative form, the same or a similar type casing would be provided, similarly dimensioned to be positioned over the neck of the vase and accommodating the threaded engagement of the cap with the neck of the vase.

An important feature of any type cartridge that is used is that it can be quickly and easily positioned for activation, and easily replaced when exhausted. This greatly facilitates convenience of usage of the system by the customer.

It will thus be seen that the objects of the invention have been accomplished. The fragrance emitting plant-watering system is of simple construction, essentially comprising three separate components which can be easily and quickly assembled. The cap is specially formed to provide support for a potted plant, and is mounted for adjustment on the vase to expose the fragrance emitting gel in varying amounts. The system provides automatic self-watering of the plant while at the same time providing the additional air freshening function.

What is claimed is:

1. A plant watering container assembly comprising:
   a bottom container section having closed side and bottom walls defining a reservoir for supplying water to a plant contained in a generally funnel-shaped pot, and
   a top container section removably connected to said bottom container section in a water tight manner, said top container section including an integrally formed funnel-shaped central section extending downwardly toward but terminating substantially above said reservoir and defining a complementary funnel-shaped opening for receiving the potted plant, with the length of said funnel-shaped central section being such that the bottom of the section extends below the pot when the latter is supported in position,
   whereby, in the event the container is tipped or turned on its side, water in the reservoir is trapped outwardly of said funnel-shaped central section, the water tight connection between the top and bottom container sections precluding water passing outwardly of the container through the funnel-shaped central section.

2. The container assembly of claim 1, wherein said funnel-shaped section is formed with an annular shoulder adjacent to the top surface of said top container section, said pot having a top annular flange adapted to fit snugly in said annular shoulder when the pot is positioned in the funnel-shaped central section.

* * * * *